United States Patent
Sasaki

(10) Patent No.: US 10,640,703 B2
(45) Date of Patent: May 5, 2020

(54) SEMICONDUCTOR NANOPARTICLE, DISPERSION LIQUID, FILM, AND METHOD OF PRODUCING SEMICONDUCTOR NANOPARTICLE

(71) Applicant: FUJIFILM Corporation, Tokyo (JP)

(72) Inventor: Tsutomu Sasaki, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/906,781

(22) Filed: Feb. 27, 2018

(65) Prior Publication Data

US 2018/0187074 A1 Jul. 5, 2018

Related U.S. Application Data

(63) Continuation of application No. PCT/JP2016/074134, filed on Aug. 18, 2016.

(30) Foreign Application Priority Data

Aug. 31, 2015 (JP) ................................. 2015-170307

(51) Int. Cl.
| | |
|---|---|
| *C09K 11/56* | (2006.01) |
| *B82Y 5/00* | (2011.01) |
| *C01B 25/08* | (2006.01) |
| *C09K 11/06* | (2006.01) |
| *C09K 11/70* | (2006.01) |
| *B82Y 30/00* | (2011.01) |
| *B82Y 20/00* | (2011.01) |
| *B82Y 40/00* | (2011.01) |

(52) U.S. Cl.
CPC .............. *C09K 11/565* (2013.01); *B82Y 5/00* (2013.01); *C01B 25/087* (2013.01); *C09K 11/06* (2013.01); *C09K 11/70* (2013.01); *B82Y 20/00* (2013.01); *B82Y 30/00* (2013.01); *B82Y 40/00* (2013.01); *Y10S 977/774* (2013.01); *Y10S 977/816* (2013.01); *Y10S 977/818* (2013.01); *Y10S 977/819* (2013.01); *Y10S 977/824* (2013.01); *Y10S 977/892* (2013.01); *Y10S 977/95* (2013.01)

(58) Field of Classification Search
CPC ....................................................... H01L 51/42
USPC ......................................................... 257/14
See application file for complete search history.

(56) References Cited

U.S. PATENT DOCUMENTS

| 7,687,800 B1 | 3/2010 | Kar et al. |
| 2009/0230382 A1 | 9/2009 | Banin et al. |
| 2014/0264172 A1 | 9/2014 | Daniels et al. |
| 2015/0287878 A1 | 10/2015 | Ono et al. |
| 2016/0190452 A1 | 6/2016 | Ono et al. |

FOREIGN PATENT DOCUMENTS

| JP | 2008-544013 A | 12/2008 | |
| JP | 5137825 B2 | 2/2013 | |
| JP | 2014-093327 | * 5/2014 | ............. H01L 51/42 |
| JP | 2014-93327 A | 5/2014 | |
| JP | 2014-143397 A | 8/2014 | |
| JP | 2015-70204 A | 4/2015 | |

OTHER PUBLICATIONS

Aharoni et al., "Synthesis of InAs/CdSe/ZnSe Core/Shell1/Shell2 Structures with Bright and Stable Near-Infrared Fluorescence," Journal of American Chemical Society, vol. 128, No. 1, 2006 (Published on Web Dec. 7, 2005), pp. 257-264.

Geyer et al., "Charge Transport in Mixed CdSe and CdTe Colloidal Nanocrystal Films," Physical Reviews B, vol. 82, 2010 (Published Oct. 7, 2010), pp. 155201-1 to 155201-8.

International Preliminary Report on Patentability and Written Opinion of the International Searching Authority (forms PCT/IB/373 and PCT/ISA/237 ), dated Mar. 6, 2018, for corresponding International Application No. PCT/JP2016/074134, with an English translation of the Written Opinion.

International Search Report (form PCT/ISA/210), dated Sep. 20, 2016, for corresponding International Application No. PCT/JP2016/074134, with an English translation.

Kim et al., "Highly Luminescent InP/GaP/ZnS Nanocrystals and Their Application to White Light-Emitting Diodes," Journal of American Chemical Society, vol. 134, No. 8, 2012 (Published Feb. 3, 2012), pp. 3804-3809.

Kim et al., "Highly Luminescing Multi-shell Semiconductor Nanocrystals InP/ZnSe/ZnS," Applied Physics Letters, vol. 101, 2012 (Published online Aug. 14, 2012), pp. 073107-1 to 073107-4 (5 pages total).

Luther et al., "Structural, Optical, and Electrical Properties of Self-Assembled Films of PbSe Nanocrystals Treated with 1,2-Ethanedithiol," American Chemical Society Nano, vol. 2, No. 2, 2008, (Published online Jan. 31, 2008), pp. 271-280.

Murray et al., "Synthesis and Characterization of Nearly Monodisperse CdE (E = S, Se, Te) Semiconductor Nanocrystallites," J. Am. Chem. Soc., vol. 115, 1993, pp. 8706-8715.

Japanese Office Action, dated Feb. 19, 2019, for corresponding Japanese Application No. 2017-537734, with an English translation.

* cited by examiner (Continued)

*Primary Examiner* — Khanh T Nguyen

(74) *Attorney, Agent, or Firm* — Birch, Stewart, Kolasch & Birch, LLP

(57) ABSTRACT

An object of the present invention is to provide a semiconductor nanoparticle having high emission efficiency and excellent durability; a method of producing the same; and a dispersion liquid and a film obtained by using a semiconductor nanoparticle. The semiconductor nanoparticle of the present invention is a semiconductor nanoparticle in which oxygen, zinc, and sulfur are detected by X-ray photoelectron spectroscopy analysis and a peak ($I_{CH3}$) which is derived from a hydrocarbon group and present in a range of 2800 cm$^{-1}$ to 3000 cm$^{-1}$ and a peak ($I_{COO}$) which is derived from COO$^-$ and present in a range of 1400 cm$^{-1}$ to 1600 cm$^{-1}$ are detected by Fourier transform infrared spectroscopy analysis.

28 Claims, No Drawings

SEMICONDUCTOR NANOPARTICLE, DISPERSION LIQUID, FILM, AND METHOD OF PRODUCING SEMICONDUCTOR NANOPARTICLE

CROSS-REFERENCE TO RELATED APPLICATIONS

This application is a Continuation of PCT International Application No. PCT/JP2016/074134 filed on Aug. 18, 2016, which claims priority under 35 U.S.C. § 119(a) to Japanese Patent Application No. 2015-170307 filed on Aug. 31, 2015. The above application is hereby expressly incorporated by reference, in its entirety, into the present application.

BACKGROUND OF THE INVENTION

1. Field of the Invention

The present invention relates to a semiconductor nanoparticle, a dispersion liquid, a film, and a method of producing a semiconductor nanoparticle.

2. Description of the Related Art

A colloidal semiconductor nanoparticle (hereinafter, also referred to as a "quantum dot") at a level of a single nano size which is obtained in a solution containing a metal element according to a chemical synthesis method has begun to be practically applied as a fluorescent substance in a wavelength conversion film used for some display applications, and applications thereof to biological labels, light emitting diodes, solar cells, and thin film transistors have also been expected.

After suggestion of a hot soap method (also referred to as a hot injection method) which is a chemical synthesis method of quantum dots in "Synthesis and Characterization of Nearly Monodisperse CdE (E=S, Se, Te) Semiconductor Nanocrystallites" J. Am. Chem. Soc., written by C. B. Murray et al., No. 115, pp. 8706 to 8715 (1993), the research on quantum dots has been actively performed around the world.

Further, the examination of the quantum dots was performed mainly on a Group II-VI semiconductor containing a Cd element or a Pb element at the time of initial research, but the research of quantum dots which do not contain a Cd element or a Pb element has been recently suggested since the Cd element and the Pb element are substances regulated as Restriction on Hazardous Substances (Rohs) or the like (for example, JP5137825B and "Highly Luminescent InP/GaP/ZnS Nanocrystals and Their Application to White Light-Emitting Diodes" Journal of the American Chemical Society 134, written by S. Kim et al., 3804-3809 (2012).

As a technique of improving properties of a semiconductor film formed of an aggregate of quantum dots, it has been reported that the electrical conductivity is improved by substituting a ligand molecule bonded to a quantum dot (for example, approximately at 2 nm to 10 nm) with a shorter ligand molecule (for example, see "Charge transport in mixed CdSe and DcTe colloidal nanocrystal films" written by S. Geyer et al., Physical Review B (2010) and "Structural, Optical, and Electrical Properties of Self-Assembled Films of PbSe Nanocrystals Treated with 1,2-Ethanedithiol" ACS Nano (2008)).

Further, JP2014-143397A discloses "a method of producing a semiconductor film including: a semiconductor quantum dot aggregate forming step of forming an aggregate of semiconductor quantum dots by applying a semiconductor quantum dot containing a metal atom, a first ligand coordinated to the semiconductor quantum dot, and a semiconductor quantum dot dispersion liquid containing a first solvent onto a substrate; and a ligand exchanging step of exchanging the first ligand coordinated to the semiconductor quantum dot with a second ligand agent by applying a ligand agent solution which contains a second solvent and the second ligand agent that has a shorter molecular chain length than that of the first ligand and contains thiocyanate ions and metal ions onto the aggregate" ([Claim 8]).

SUMMARY OF THE INVENTION

The present inventors performed examination on the techniques for ligand exchange described in JP2014-143397, "Charge transport in mixed CdSe and DcTe colloidal nanocrystal films" written by S. Geyer et al., Physical Review B (2010), and "Structural, Optical, and Electrical Properties of Self-Assembled Films of PbSe Nanocrystals Treated with 1,2-Ethanedithiol" ACS Nano (2008) for the purpose of improving emission efficiency. As the result, it was found that the emission efficiency of semiconductor nanoparticles to be obtained deteriorates in some cases or emission stability (hereinafter, also referred to as "durability") with respect to infrared rays or the like deteriorates in some cases depending on the type of ligand to be newly coordinated through ligand exchange.

Here, an object of the present invention is to provide a semiconductor nanoparticle having high emission efficiency and excellent durability; a method of producing the same; and a dispersion liquid and a film obtained by using a semiconductor nanoparticle.

As the result of intensive examination conducted by the present inventors in order to achieve the above-described object, it was found that the emission efficiency is high and the durability is excellent in a case where the semiconductor nanoparticle obtained by ligand exchange or introduction of a ligand is a semiconductor nanoparticle in which a predetermined element is detected by X-ray photoelectron spectroscopy analysis and a predetermined peak is detected by Fourier transform infrared spectroscopy analysis.

In other words, it was found that the above-described object can be achieved by the following configurations.

[1] A semiconductor nanoparticle, in which oxygen, zinc, and sulfur are detected by X-ray photoelectron spectroscopy analysis, and a peak ($I_{CH3}$) which is derived from a hydrocarbon group and present in a range of 2800 $cm^{-1}$ to 3000 $cm^{-1}$ and a peak ($I_{COO}$) which is derived from $COO^-$ and present in a range of 1400 $cm^{-1}$ to 1600 $cm^{-1}$ are detected by Fourier transform infrared spectroscopy analysis.

[2] The semiconductor nanoparticle according to [1], in which a molar ratio of oxygen to sulfur which is acquired by X-ray photoelectron spectroscopy analysis satisfies Formula (1), and a molar ratio of oxygen to zinc which is acquired by X-ray photoelectron spectroscopy analysis satisfies Formula (2).

$$0.20 \leq O/S \leq 0.80 \tag{1}$$

$$0.30 \leq O/Zn \leq 1.10 \tag{2}$$

[3] The semiconductor nanoparticle according to [1] or [2], in which a ratio of peak intensity between the peak ($I_{CH3}$) and the peak ($I_{COO}$) satisfies Formula (3).

$$0.22 \leq I_{COO}/I_{CH3} \leq 0.42 \tag{3}$$

[4] The semiconductor nanoparticle according to any one of [1] to [3], in which two or more kinds of ligands are coordinated.

[5] The semiconductor nanoparticle according to [4], in which both of a ligand A which is represented by Formula (A) and contains a carboxyl group and a ligand B which is represented by Formula (B) and contains a mercapto group are coordinated.

$$R^1\text{—COOH} \tag{A}$$

$$R^2\text{—SH} \tag{B}$$

Here, $R^1$ and $R^2$ in Formulae (A) and (B) each independently represent an organic group.

[6] The semiconductor nanoparticle according to [5], in which both of $R^1$ and $R^2$ in Formulae (A) and (B) represent a linear aliphatic hydrocarbon group.

[7] The semiconductor nanoparticle according to [6], in which both of $R^1$ and $R^2$ in Formulae (A) and (B) represent an aliphatic hydrocarbon group having 8 to 25 carbon atoms.

[8] The semiconductor nanoparticle according to any one of [5] to [7], in which the ligand A is at least one ligand selected from the group consisting of decanoic acid, lauric acid, myristic acid, palmitic acid, stearic acid, behenic acid, oleic acid, and erucic acid, and the ligand B is at least one ligand selected from the group consisting of dodecanethiol, octanethiol, decanethiol, tetradecanethiol, hexadecanethiol, HS—(CH2)m-OH (in the formula, m represents an integer of 11 to 16), and HS—(CH2)m-(O—CH2CH2)n-OCH3 (in the formula, m represents an integer of 11 to 16, and n represents an integer of 3 to 6).

[9] The semiconductor nanoparticle according to [8], in which the ligand A is oleic acid, and the ligand B is dodecanethiol.

[10] The semiconductor nanoparticle according to any one of [1] to [9], comprising: a core which contains a Group III element and a Group V element; and a shell which contains a Group II element and a Group VI element that cover at least a part of a surface of the core.

[11] The semiconductor nanoparticle according to any one of [1] to [9], comprising: a core which contains a Group III element and a Group V element; a first shell which covers at least a part of a surface of the core; and a second shell which covers at least a part of the first shell.

[12] The semiconductor nanoparticle according to [10] or [11], in which the Group III element contained in the core is In, and the group V element contained in the core is any of P, N, and As.

[13] The semiconductor nanoparticle according to [12], in which the Group III element contained in the core is In, and the Group V element contained in the core is P.

[14] The semiconductor nanoparticle according to any one of [10] to [13], in which the core further contains a Group II element.

[15] The semiconductor nanoparticle according to [14], in which the Group II element contained in the core is Zn.

[16] The semiconductor nanoparticle according to any one of [11] to [15], in which the first shell contains a Group II element or a Group III element.

Here, in a case where the first shell contains a Group III element, the Group III element contained in the first shell is a Group III element different from the Group III element contained in the core.

[17] The semiconductor nanoparticle according to any one of [11] to [16], in which the first shell is a Group II-VI semiconductor which contains a Group II element and a Group VI element or a Group III-V semiconductor which contains a Group III element and a Group V element.

Here, in a case where the first shell is the Group III-V semiconductor, the Group III element contained in the Group III-V semiconductor is a Group III element different from the Group III element contained in the core.

[18] The semiconductor nanoparticle according to [17], in which, in a case where the first shell is the Group II-VI semiconductor, the Group II element is Zn and the Group VI element is Se or S, and in a case where the first shell is the Group III-V semiconductor, the Group III element is Ga and the Group V element is P.

[19] The semiconductor nanoparticle according to [17], in which the first shell is the Group III-V semiconductor, the Group III element is Ga, and the Group V element is P.

[20] The semiconductor nanoparticle according to any one of [11] to [19], in which the second shell is a Group II-VI semiconductor which contains a Group II element and a Group VI element or a Group III-V semiconductor which contains a Group III element and a Group V element.

[21] The semiconductor nanoparticle according to [20], in which the second shell is the Group II-VI semiconductor, the Group II element is Zn, and the Group VI element is S.

[22] The semiconductor nanoparticle according to any one of [11] to [21], in which the core, the first shell, and the second shell are respectively a crystal system having a zinc blende structure.

[23] The semiconductor nanoparticle according to any one of [11] to [22], in which, among the core, the first shell, and the second shell, a band gap of the core is the smallest, and the core and the first shell respectively have a type 1 band structure.

[24] A dispersion liquid comprising: the semiconductor nanoparticle according to any one of [1] to [23].

[25] A film comprising: the semiconductor nanoparticle according to any one of [1] to [23].

[26] A method of producing a semiconductor nanoparticle for synthesizing the semiconductor nanoparticle according to [1], comprising: a mixing step of mixing a semiconductor nanoparticle QD to which one or both of a ligand A which is represented by Formula (A) and contains a carboxyl group and a ligand B which is represented by Formula (B) and contains a mercapto group are not coordinated, the ligand A, and the ligand B.

$$R^1\text{—COOH} \tag{A}$$

$$R^2\text{—SH} \tag{B}$$

Here, $R^1$ and $R^2$ in Formulae (A) and (B) each independently represent an organic group.

[27] The method of producing a semiconductor nanoparticle according to [26], in which the semiconductor nanoparticle QD, the ligand A, and the ligand B are mixed at a molar ratio that satisfies Formulae (4) and (5).

$$0.1 \le (\text{ligand } A/\text{ligand } B) \le 10 \tag{4}$$

$$10 \le \{\text{semiconductor nanoparticle } QD/(\text{ligand } A/\text{ligand } B)\} \le 1000 \tag{5}$$

[28] The method of producing a semiconductor nanoparticle according to [26], in which the semiconductor nanoparticle QD, the ligand A, and the ligand B are mixed at a molar ratio that satisfies Formulae (4') and (5').

$$0.5 < (\text{ligand } A/\text{ligand } B) < 5 \tag{4'}$$

$$100 < \{\text{semiconductor nanoparticle } QD/(\text{ligand } A/\text{ligand } B)\} < 300 \tag{5'}$$

[29] The method of producing a semiconductor nanoparticle according to any one of [26] to [28], in which the semiconductor nanoparticle QD, the ligand A, and the ligand B are mixed in a temperature range of 20° C. to 100° C.

[30] The method of producing a semiconductor nanoparticle according to any one of [26] to [29], in which the semiconductor nanoparticle QD, the ligand A, and the ligand B are mixed under a light shielding condition and/or in a nitrogen atmosphere.

[31] The method of producing a semiconductor nanoparticle according to any one of [26] to [30], in which the mixing step is performed for 8 hours or longer.

[32] The method of producing a semiconductor nanoparticle according to any one of [26] to [31], further comprising: a step of leaving the mixture to rest for 8 hours or longer after the mixing step.

According to the present invention, it is possible to provide a semiconductor nanoparticle having high emission efficiency and excellent durability; a method of producing the same; and a dispersion liquid and a film obtained by using a semiconductor nanoparticle.

DESCRIPTION OF THE PREFERRED EMBODIMENTS

Hereinafter, the present invention will be described in detail.

The description of constituent elements below will be made based on representative embodiments of the present invention, but the present invention is not limited to these embodiments.

In the present specification, the numerical ranges expressed using "to" in the present specification indicate the ranges including the numerical values described before and after "to" as the lower limits and the upper limits.

[Semiconductor Nanoparticle]

A semiconductor nanoparticle of the present invention is a semiconductor nanoparticle in which oxygen, zinc, and sulfur are detected by X-ray photoelectron spectroscopy (hereinafter, also referred to as "XPS") and a peak ($I_{CH3}$) which is derived from a hydrocarbon (C—H stretching) group and present in a range of 2800 cm$^{-1}$ to 3000 cm$^{-1}$ and a peak ($I_{COO}$) which is derived from COO$^-$ (C=O stretching and C—O stretching) and present in a range of 1400 cm$^{-1}$ to 1600 cm$^{-1}$ are detected by Fourier transform infrared spectroscopy (hereinafter, also referred to as "FT-IR").

In the present invention, it is determined whether oxygen, zinc, and sulfur are detected by the detection method using XPS in a case where measurement is carried out under the following measurement conditions.

Further, the molar ratio of oxygen to sulfur and the molar ratio of oxygen to zinc acquired from XPS are acquired by correcting the ratio of the peak intensity of an oxygen element to the peak intensity of a sulfur atom or a zinc atom contained in the semiconductor nanoparticle with a relative sensitivity coefficient for each element. The relative sensitivity coefficient is acquired by measuring measurement elements (measurement trajectory) described later related to standard samples whose compositions have been known (Journal of Surface Analysis, Vol. 12, No. 3, pp. 357 (2005)).

Further, the peak intensity indicates the area intensity obtained by subtracting the background from the peak observed under the following measurement conditions and integrating the area of the peak with respect to the energy.

Further, the XPS measurement is performed by using a sample obtained by coating a non-doped Si substrate with a dispersion liquid (solvent: toluene) containing semiconductor nanoparticles and drying the substrate.

<Measurement Conditions>

Measuring device: Quantera SXM type XPS (manufactured by ULVAC-PHI, Inc.)

X-ray source: Al-Kα ray (analytic diameter: 100 μm, 25 W, 15 kV)

Extraction angle of photoelectrons: 45° C.

Measurement range: 300 μm×300 μm

Correction: charging correction using combination of electron gun and low-speed ion gun Measurement elements (measurement trajectory): C (1s), N (1s), O (1s), Si (2p), P (2p), S (2p), Cl (2p), Zn (2p3/2), Ga (2p3/2), In (3d5/2)

In the present invention, it is determined whether the peak ($I_{CH3}$) and the peak ($I_{COO}$) are detected by the detection method using FT-IR in a case where measurement is carried out under the following measurement conditions.

Further, the ratio of the peak intensity between the peak ($I_{CH3}$) and the peak ($I_{COO}$) indicates a ratio of the maximum peak intensity of the peak ($I_{COO}$) to the maximum peak intensity of the peak ($I_{CH3}$) which is obtained by subtracting the background from each peak to be observed under the following measurement conditions.

Further, the FT-IR measurement is performed by using a sample obtained by coating a non-doped Si substrate with a dispersion liquid (solvent: toluene) containing semiconductor nanoparticles and drying the substrate in a nitrogen atmosphere.

<Measurement Conditions>

Measuring device: Nicolet 4700 (diamond ATR arrangement, manufactured by Thermo Fisher Scientific)

Detector: DTGS KBr

Light source: IR

Measurement accessory: Transmission E.S.P.

Beam splitter: KBr

Measured wave number: 400 to 4000 cm$^{-1}$

Measured interval: 1.928 cm$^{-1}$

Number of times of scanning: 32

Resolution: 4

In the semiconductor nanoparticle of the present invention, it is preferable that the molar ratio of oxygen to sulfur obtained from XPS satisfies Formula (1) and the molar ratio of oxygen to zinc obtained from XPS satisfies Formula (2), from the viewpoint of further increasing the emission efficiency and further improving the durability.

The specific reason why the emission efficiency is further increased and the durability is further improved by satisfying Formulae (1) and (2) is unclear, but it is assumed that the reason is because a carboxyl group is coordinated to a portion which is generated on the outermost surface of the semiconductor nanoparticle and to which a mercapto group cannot be coordinated or a defect generated by being accompanied by this portion.

$$0.20 \leq O/S \leq 0.80 \tag{1}$$

$$0.30 \leq O/Zn \leq 1.10 \tag{2}$$

In the semiconductor nanoparticle of the present invention, from the viewpoint of further improving the durability, it is preferable that the ratio of the peak intensity between the peak ($I_{CH3}$) and the peak ($I_{COO}$) to be detected by FT-IR satisfies Formula (3).

It is considered that the durability is improved because reinforcement to the defect site using a carboxyl group and a mercapto group has proceeded in an optimum amount with respect to the state of the surface of the semiconductor nanoparticle in a case where the ratio of the peak intensity satisfies Formula (3).

$$0.22 \leq I_{COO}/I_{CH3} \leq 0.42 \quad (3)$$

[Ligand]

In the semiconductor nanoparticle of the present invention, from the viewpoints of further increasing the emission efficiency and further improving the durability, it is preferable that two or more kinds of ligands are coordinated. Specifically, it is more preferable that both of a ligand A which is represented by Formula (A) and contains a carboxyl group and a ligand B which is represented by Formula (B) and contains a mercapto group are coordinated.

$$R^1\text{—COOH} \quad (A)$$

$$R^2\text{—SH} \quad (B)$$

Here, $R^1$ and $R^2$ in Formulae (A) and (B) each independently represent an organic group.

Further, "coordinated" means that a ligand chemically affects the surface of the semiconductor nanoparticle. For example, in a case where at least a part of the surface of the semiconductor nanoparticle has a ligand, a coordinate bond may not necessarily be formed.

Examples of the organic group include a substituent and a monovalent hydrocarbon group which may have a heteroatom, and specific examples thereof include an aliphatic hydrocarbon group such as an alkyl group and a cycloalkyl group; an aromatic hydrocarbon group such as an aryl group; and an unsaturated hydrocarbon group such as a vinyl group and an allyl group.

As the organic group represented by R1 and R2 in Formulae (A) and (B), from the viewpoint of preventing aggregation, a linear aliphatic hydrocarbon group is preferable and an aliphatic hydrocarbon group having 8 to 25 carbon atoms is more preferable.

Specific examples of the ligand A represented by Formula (A) include decanoic acid, lauric acid, myristic acid, palmitic acid, stearic acid, behenic acid, oleic acid, and erucic acid, and these may be used alone or in combination of two or more kinds thereof.

Further, specific examples of the ligand B represented by Formula (B) include dodecanethiol, octanethiol, decanethiol, tetradecanethiol, hexadecanethiol, HS—(CH2)m-OH (in the formula, m represents an integer of 11 to 16), and HS—(CH2)m-(O—CH2CH2)n-OCH3 (in the formula, m represents an integer of 11 to 16, and n represents an integer of 3 to 6), and these may be used alone or in combination of two or more kinds thereof.

Among the examples described above, an aspect in which at least oleic acid is used as the ligand A and at least dodecanethiol is used as the ligand B is preferable because these are general-purpose materials and the ligands can be coordinated at a high density.

The particle shape of the semiconductor nanoparticle of the present invention is not particularly limited as long as oxygen, zinc, and sulfur are detected by XPS and the peak ($I_{CH3}$) and the peak ($I_{COO}$) are detected by FT-IR, and preferred examples thereof include core shell shapes such as a shape (single shell shape) having a core which contains a Group III element and a Group V element and a shell which contains a Group II element and a Group VI element that cover at least a part of the surface of the core; and a shape (multi-shell shape) having a core which contains a Group III element and a Group V element, a first shell which covers at least a part of the surface of the core, and a second shell which covers at least a part of the first shell. Among these, a multi-shell shape is preferable.

[Core]

In a case where the semiconductor nanoparticle of the present invention is a core shell particle, it is preferable that the core contained in the core shell particle of the present invention is a so-called Group III-V semiconductor that contains a Group III element and a Group V element.

<Group III Element>

Specific examples of the Group III element include indium (In), aluminum (Al), and gallium (Ga). Among these, In is preferable.

<Group V Element>

Specific examples of the Group V element include phosphorus (P), nitrogen (N), and arsenic (As). Among these, P is preferable.

In the present invention, a Group III-V semiconductor obtained by appropriately combining the Group III element and the Group V element exemplified above can be used as the core, but InP, InN, or InAs is preferable from the viewpoint that the emission efficiency is further increased, the emission half-width is narrowed, and a clear exciton peak is obtained. Among these, from the viewpoint of further increasing the emission efficiency, InP is more preferable.

In the present invention, it is preferable that the core further contains a Group II element in addition to the Group III element and the Group V element described above. Particularly in a case where the core is InP, the lattice constant is decreased by doping Zn as the Group II element and the lattice matching performance with a shell (for example, GaP, ZnS, or the like described below) having a smaller lattice constant than that of InP becomes excellent.

[Shell]

In a case where the semiconductor nanoparticle of the present invention is a core shell particle having a single shell shape, it is preferable that the shell is a material that covers at least a part of the surface of the core and is a so-called Group II-VI semiconductor that contains a Group II element and a Group VI element.

Here, in the present invention, it is possible to confirm whether at least a part of the surface of the core is covered with the shell based on composition distribution analysis according to energy dispersive X-ray spectroscopy (EDX) using a transmission electron microscope (TEM).

<Group II Element>

Specific examples of the Group II element include zinc (Zn), cadmium (Cd), and magnesium (Mg). Among these, Zn is preferable.

<Group VI Element>

Further, specific examples of the Group VI element include sulfur (S), oxygen (O), selenium (Se), and tellurium (Te). Among these, S or Se is preferable and S is more preferable.

In the present invention, a Group II-VI semiconductor obtained by appropriately combining the Group II element and the Group VI element described above can be used as the shell, but it is preferable that the shell is a crystal system which is the same as or similar to the core described above. Specifically, ZnS or ZnSe is preferable, and ZnS is more preferable from the viewpoint of safety or the like.

[First Shell]

In a case where the semiconductor nanoparticle of the present invention is a core shell particle having a multi-shell shape, the first shell is a material that covers at least a part of the surface of the core.

Here, in the present invention, it is possible to confirm whether at least a part of the surface of the core is covered with the first shell based on composition distribution analysis according to energy dispersive X-ray spectroscopy (EDX) using a transmission electron microscope (TEM).

In the present invention, from the viewpoint of easily suppressing defects of the interface between the core and the first shell, it is preferable that the first shell contains a Group II element or a Group III element.

Here, in a case where the first shell contains a Group III element, the Group III element contained in the first shell is a Group III element different from the Group III element contained in the core described above.

Further, in addition to a Group II-VI semiconductor and a Group III-V semiconductor described below, a Group III-VI semiconductor (such as $Ga_2O_3$, $Ga_2S_3$, or the like) containing a Group III element and a Group VI element is exemplified as the first shell containing a Group II element or a Group III element.

In the present invention, from the viewpoint of obtaining an excellent crystal phase with less defects, it is preferable that the first shell is a Group II-VI semiconductor containing a Group II element and a Group VI element or a Group III-V semiconductor containing a Group III element and a Group V element and more preferable that the first shell is a Group III-V semiconductor in which a difference in lattice constant between the core described above and the first shell is small.

Here, in a case where the first shell is a Group III-V semiconductor, the Group III element contained in the Group III-V semiconductor is a Group III element different from the Group III element contained in the core described above.

<Group II-VI Semiconductor>

Specific examples of the Group II element contained in the Group II-VI semiconductor include zinc (Zn), cadmium (Cd), and magnesium (Mg). Among these, Zn is preferable.

Further, specific examples of the Group VI element contained in the Group II-VI semiconductor include sulfur (S), oxygen (O), selenium (Se), and tellurium (Te). Among these, S or Se is preferable and S is more preferable.

A Group II-VI semiconductor obtained by appropriately combining the Group II element and the Group VI element described above can be used as the first shell, but it is preferable that the first shell is a crystal system (for example, a zinc blende structure) which is the same as or similar to the core described above. Specifically, ZnSe, ZnS, or a mixed crystal of these is preferable and ZnSe is more preferable.

<Group III-V Semiconductor>

Specific examples of the Group III element contained in the Group III-V semiconductor include indium (In), aluminum (Al), and gallium (Ga). Among these, Ga is preferable. As described above, the Group III element contained in the Group III-V semiconductor is a Group III element different from the Group III element contained in the core described above. For example, in a case where the Group III element contained in the core is In, the Group III element contained in the Group III-V semiconductor is Al, Ga, or the like.

Further, specific examples of the Group V element contained in the Group III-V semiconductor include phosphorus (P), nitrogen (N), and arsenic (As). Among these, P is preferable.

A Group III-V semiconductor obtained by appropriately combining the Group III element and the Group V element described above can be used as the first shell, but it is preferable that the first shell is a crystal system (for example, a zinc blende structure) which is the same as or similar to the core described above. Specifically, GaP is preferable.

In the present invention, from the viewpoint of reducing defects of the surface of the core shell particle to be obtained, it is preferable that a difference in lattice constant between the above-described core and the first shell is small. Specifically, it is preferable that the difference in lattice constant between the above-described core and the first shell is 10% or less.

Specifically, in a case where the above-described core is InP, it is preferable that the first shell is ZnSe (difference in lattice constant: 3.4%) or GaP (difference in lattice constant: 7.1%) as described above. Particularly, it is more preferable that the first shell is the same Group III-V semiconductor as the core and the Group III-V semiconductor is GaP from the viewpoint that a mixed crystal state can be easily made on the interface between the core and the first shell.

In the present invention, in a case where the first shell is a Group III-V semiconductor, the first shell may contain or dope another element (for example, the Group II element or the Group VI element described above) within the range that does not affect the magnitude correlation (core<first shell) of the band gap between the core and the first shell. Similarly, in a case where the first shell is a Group II-VI semiconductor, the first shell may contain or dope another element (for example, the Group III element or the Group V element described above) within the range that does not affect the magnitude correlation (core<first shell) of the band gap between the core and the first shell.

[Second Shell]

In a case where the semiconductor nanoparticle of the present invention is a core shell particle having a multi-shell shape, the second shell is a material that covers at least a part of the surface of the first shell described above.

Here, in the present invention, it is possible to confirm whether at least a part of the surface of the first shell is covered with the second shell based on composition distribution analysis according to energy dispersive X-ray spectroscopy (EDX) using a transmission electron microscope (TEM).

In the present invention, from the viewpoints of suppressing defects of the interface between the first shell and the second shell and obtaining an excellent crystal phase with less defects, it is preferable that the second shell is a Group II-VI semiconductor containing a Group II element and a Group VI element or a Group III-V semiconductor containing a Group III element and a Group V element. Further, from the viewpoints of high reactivity of the material itself and easily obtaining a shell with excellent crystallinity, it is more preferable that the second shell is a Group II-VI semiconductor.

Examples of the Group II element, the Group VI element, the Group III element, and the Group V element include those described in the section of the first shell.

A Group II-VI semiconductor obtained by appropriately combining the Group II element and the Group VI element described above can be used as the second shell, but it is preferable that the second shell is a crystal system (for example, a zinc blende structure) which is the same as or similar to the core described above. Specifically, ZnSe, ZnS, or a mixed crystal of these is preferable and ZnS is more preferable.

A Group III-V semiconductor obtained by appropriately combining the Group III element and the Group V element described above can be used as the second shell, but it is preferable that the second shell is a crystal system (for example, a zinc blende structure) which is the same as or similar to the core described above. Specifically, GaP is preferable.

In the present invention, from the viewpoint of reducing defects of the surface of the core shell particle to be obtained, it is preferable that a difference in lattice constant between the first shell and the second shell described above is small. Specifically, it is preferable that the difference in lattice constant between the first shell and the second shell described above is 10% or less.

Specifically, in a case where the above-described first shell is GaP, it is preferable that the second shell is ZnSe (difference in lattice constant: 3.8%) or ZnS (difference in lattice constant: 0.8%) as described above and more preferable that the second shell is ZnS.

In the present invention, in a case where the second shell is a Group II-VI semiconductor, the second shell may contain or dope another element (for example, the Group III element or the Group V element described above) within the range that does not affect the magnitude correlation (core<second shell) of the band gap between the core and the second shell. Similarly, in a case where the second shell is a Group III-V semiconductor, the second shell may contain or dope another element (for example, the Group II element or the Group VI element described above) within the range that does not affect the magnitude correlation (core<second shell) of the band gap between the core and the second shell.

In the present invention, from the viewpoint that epitaxial growth becomes easy and defects of an interface between layers are easily suppressed, it is preferable that each of the core, the first shell, and the second shell described above is a crystal system having a zinc blende structure.

In the present invention, from the viewpoint that the probability of excitons staying in the core becomes higher and the emission efficiency is further increased, it is preferable that the band gap of the core from among the core, the first shell, and the second shell is the smallest and the core and the first shell are core shell particles having a type 1 (type I) band structure.

[Average Particle Diameter]

From the viewpoints of easily synthesizing particles having a uniform size and easily controlling the emission wavelength using quantum size effects, the average particle diameter of the semiconductor nanoparticles of the present invention is preferably 2 nm or greater and more preferably 10 nm or less.

Here, the average particle diameter is a value obtained by directly observing at least 20 particles using a transmission electron microscope, calculating the diameters of circles having the same area as the projected area of the particles, and arithmetically averaging these values.

[Method of Producing Core Shell Particle]

A method of producing a semiconductor nanoparticle that includes synthesizing the semiconductor nanoparticle of the present invention (hereinafter, also referred to as the "production method of the present invention") is a method of producing a semiconductor nanoparticle that includes a mixing step of mixing a semiconductor nanoparticle QD to which any or both of the ligand A and the ligand B are not coordinated, the ligand A, and the ligand B.

Further, the production method of the present invention may include a leaving step of leaving (standing) the mixture to rest after the mixing step. In addition, the coordination of the ligand A and the ligand B to the semiconductor nanoparticle QD may proceed in the mixing step or in the leaving step.

Here, the ligand A and the ligand B are the same as those described in the section of the semiconductor nanoparticle of the present invention described above.

The semiconductor nanoparticle QD is a known semiconductor nanoparticle of the related art to which any or both of the ligand A and the ligand B are not coordinated and is also a semiconductor nanoparticle in which any or both of the peak ($I_{CH3}$) and the peak ($I_{COO}$) are not detected by FT-IR.

According to the production method of the present invention, it is preferable that the semiconductor nanoparticle QD, the ligand A, and the ligand B are mixed at a molar ratio that satisfies Formulae (4) and (5) because the emission efficiency of the semiconductor nanoparticle to be prepared is further increased; and more preferable that the semiconductor nanoparticle QD, the ligand A, and the ligand B are mixed at a molar ratio that satisfies Formulae (4') and (5') because the durability of the semiconductor nanoparticle to be synthesized is further improved.

$$0.1 \leq (\text{ligand } A/\text{ligand } B) \leq 10 \quad (4)$$

$$0.5 \leq (\text{ligand } A/\text{ligand } B) \leq 5 \quad (4')$$

$$10 \leq \{\text{semiconductor nanoparticle } QD/(\text{ligand } A/\text{ligand } B)\} \leq 1000 \quad (5)$$

$$100 \leq \{\text{semiconductor nanoparticle } QD/(\text{ligand } A/\text{ligand } B)\} \leq 300 \quad (5')$$

According to the production method of the present invention, from the viewpoint that the coordination of the ligand A and the ligand B easily proceeds, the semiconductor nanoparticle QD, the ligand A, and the ligand B are mixed preferably in a temperature range of 20° C. to 100° C. and more preferably in a temperature range of 50° C. to 85° C.

Further, in a case where the production method of the present invention includes an optional leaving step, from the same viewpoint as described above, the mixture is allowed to be left preferably in a temperature range of 20° C. to 100° C. and more preferably in a temperature range of 50° C. to 85° C.

According to the production method of the present invention, from the viewpoint of suppressing defects of coordination of the ligand A and the ligand B, it is preferable that the semiconductor nanoparticle QD, the ligand A, and the ligand B are mixed under a light shielding condition and/or in a nitrogen atmosphere; and more preferable that the semiconductor nanoparticle QD, the ligand A, and the ligand B are mixed under a light shielding condition and in a nitrogen atmosphere.

Further, in a case where the production method of the present invention includes an optional leaving step, from the same viewpoint as described above, it is preferable that the mixture is allowed to be left under a light shielding condition and/or in a nitrogen atmosphere; and more preferable that the mixture is allowed to be left under a light shielding condition and in a nitrogen atmosphere.

According to the production method of the present invention, from the viewpoint that the coordination of the ligand A and the ligand B easily proceeds, the mixing step of mixing the semiconductor nanoparticle QD, the ligand A, and the ligand B is performed preferably for 8 hours or longer and more preferably for 12 to 48 hours.

From the same reason as described above, in a case where the production method of the present invention includes an arbitrary leaving step, the leaving step is performed preferably for 8 hours or longer and more preferably for 12 to 48 hours.

[Dispersion Liquid]

The dispersion liquid of the present invention is a dispersion liquid which contains the semiconductor nanoparticle of the present invention described above.

Here, a non-polar solvent is preferable as a solvent constituting a dispersion medium of the dispersion liquid.

Examples of the non-polar solvent include aromatic hydrocarbon such as toluene; alkyl halide such as chloroform; aliphatic saturated hydrocarbon such as hexane, octane, n-decane, n-dodecane, n-hexanedecane, or n-octadecane; aliphatic unsaturated hydrocarbon such as 1-undecene, 1-dodecene, 1-hexadecene, or 1-octadecene; and trioctylphosphine.

The content (concentration) of the semiconductor nanoparticle of the present invention in the dispersion liquid of the present invention is preferably in a range of 0.1 to 100 mol/L and more preferably in a range of 0.1 to 1 mol/L with respect to the total mass of the dispersion liquid of the present invention.

[Film]

The film of the present invention is a film containing the semiconductor nanoparticle of the present invention described above.

Since such a film of the present invention has high emission efficiency and excellent durability, the film can be applied to a wavelength conversion film used for a display, a photoelectron conversion (or wavelength conversion) film of a solar cell, a biological label, a thin film transistor, and the like. Particularly, since the film of the present invention has excellent durability with respect to ultraviolet rays or the like, the film is suitably applied to a down conversion film or a down shift type wavelength conversion film which absorbs light in a shorter wave region than that of the absorption edge of quantum dots and emits light having a long wave.

Further, the film material serving as a base material constituting the film of the present invention is not particularly limited and may be a resin or a thin glass film.

Specific examples thereof include resin materials mainly formed of an ionomer, polyethylene, polyvinyl chloride, polyvinylidene chloride, polyvinyl alcohol, polypropylene, polyester, polycarbonate, polystyrene, polyacrylonitrile, an ethylene vinyl acetate copolymer, an ethylene-vinyl alcohol copolymer, an ethylene-methacrylic acid copolymer film, and nylon.

EXAMPLES

Hereinafter, the present invention will be described in more detail based on examples. The materials, the use amounts, the ratios, the treatment contents, and the treatment procedures described in the following examples can be changed as appropriate within the range not departing from the gist of the present invention. Therefore, the scope of the present invention should not be limitatively interpreted by the following examples.

<Synthesis of Semiconductor Nanoparticle QD>

32 mL of octadecene, 140 mg (0.48 mmol) of indium acetate, and 48 mg (0.24 mmol) of zinc chloride were added to a 32 mL flask, heated and stirred at 110° C. in a vacuum, and degassed for 90 minutes while the raw materials were sufficiently dissolved.

Next, the flask was heated to 300° C. in a nitrogen flow, and 0.24 mmol of tristrimethylsilylphosphine dissolved in approximately 4 mL of octadecene was added to the flask after the temperature of the solution was stabilized. Thereafter, the flask was heated for 120 minutes in a state in which the temperature of the solution was set to 230° C. It was confirmed that the color of the solution was red and particles (cores) were formed.

Next, 30 mg (0.18 mmol) of gallium chloride and 125 µL (0.4 mmol) of oleic acid which were dissolved in 8 mL of octadecene were added to the solution in a state in which the solution was heated to 200° C., and the solution was further heated for approximately 1 hour, and then a dispersion liquid containing a core shell particle precursor having InP (core) doped with Zn and GaP (first shell) was obtained.

Next, the dispersion liquid was cooled to room temperature, 220 mg (1.2 mmol) of zinc acetate was added thereto, the dispersion liquid was heated to 230° C., and the temperature thereof was maintained for approximately 4 hours. Next, 1.15 mL (4.85 mmol) of dodecanethiol was added to the dispersion liquid and the dispersion liquid was heated to 240° C. The obtained dispersion liquid was cooled to room temperature, 293 mg (1.6 mmol) of zinc acetate was added thereto again, the dispersion liquid was heated to 230° C., and the temperature thereof was maintained for approximately 1 hour. Next, 1.53 mL (6.5 mmol) of dodecanethiol was added to the dispersion liquid again and the dispersion liquid was heated to 240° C. After the obtained dispersion liquid was cooled to room temperature, ethanol was added thereto, and centrifugation was performed on the dispersion liquid so that particles were precipitated. The supernatant was disposed and the resultant was dispersed in a toluene solvent.

In this manner, a toluene dispersion liquid of core shell particles including InP (core) doped with Zn, GaP (first shell) covering the surface of the core, and ZnS (second shell) covering the surface of the first shell was obtained.

Examples 1 to 5 and Comparative Examples 1 to 3

<Ligand Exchange>

The concentration of the solution was adjusted such that the absorbance of the toluene dispersion liquid containing the prepared core shell particles (InP/GaP/ZnS) at an excitation wavelength of 450 nm was set to 0.2.

Next, the ligand A, the ligand B, and other ligands listed in Table 1 were added to the solution at a molar ratio listed in Table 1 while the solution was stirred, and the solution was sealed with nitrogen. In this state, the temperature of the solution was maintained at 65° C., the solution was allowed to be left for 24 hours under a light shielding condition, and the ligand exchange was promoted.

Further, in Comparative Example 2, the toluene dispersion liquid containing the prepared core shell particles was used as it was without performing the ligand exchange.

[XPS]

With each of the prepared dispersion liquids, the presence of detected oxygen, zinc, or sulfur, and the molar ratio of oxygen to sulfur and the molar ratio of oxygen to zinc were measured using XPS according to the above-described method. The results thereof are listed in Table 1.

[FT-IR]

With each of the prepared dispersion liquids, the presence of the detected peak ($I_{CH3}$) or peak ($I_{COO}$) and the ratio of the peak intensity between the peaks ($I_{COO}/I_{CH3}$) were measured using FT-IR according to the above-described method. The results thereof are listed in Table 1.

[Emission Efficiency]

<Initial Stage>

The emission intensity of each of the prepared dispersion liquids was measured using a fluorescence spectrophotometer FluoroMax-3 (manufactured by HORIBA Jobin Yvon) by adjusting the concentration thereof such that the absorbance at an excitation wavelength of 450 nm was set to 0.2. Further, the emission efficiency was calculated by performing relative comparison with a quantum dot sample whose emission efficiency was known. The obtained emission efficiency was calculated as a ratio of the number of emission photons to the number of absorption photons from excitation light. The results are listed in Table 1.

<After Irradiation with Ultraviolet Rays>

Each of the prepared dispersion liquids was irradiated with ultraviolet rays by fixing a mercury lamp (wavelength of 365 nm) at a position of 1 mW/cm². Further, the time for irradiating each solution with ultraviolet rays was set to 105 minutes and the irradiation amount was set to 8 J/cm².

Thereafter, the emission efficiency was measured in the same manner as that for the initial stage. The results are listed in Table 1.

a peak ($I_{CH3}$) which is derived from a hydrocarbon group and present in a range of 2800 cm$^{-1}$ to 3000 cm$^{-1}$ and a peak ($I_{COO}$) which is derived from COO$^-$ and present in a range of 1400 cm$^{-1}$ to 1600 cm$^{-1}$ are detected by Fourier transform infrared spectroscopy analysis, wherein a molar ratio of oxygen to sulfur which is acquired by X-ray photoelectron spectroscopy analysis satisfies Formula (1), and a molar ratio of oxygen to zinc which is acquired by X-ray photoelectron spectroscopy analysis satisfies Formula (2), $$0.20 \leq O/S \leq 0.80 \tag{1}$$

$$0.30 \leq O/Zn \leq 1.10 \tag{2}$$

TABLE 1

| Table 1 | Ligand A | Ligand B | Other ligands | Ligand A/ ligand B | Semiconductor nanoparticle QD/ (ligand A/ ligand B) | XPS Detected elements | XPS Molar ratio O/S | XPS Molar ratio O/Zn | FT-IR $I_{CH3}$ | FT-IR $I_{COO}$ | FT-IR Ratio of peak intensity $I_{COO}/I_{CH3}$ | Emission efficiency (%) Initial stage | Emission efficiency (%) After irradiation with ultraviolet rays |
|---|---|---|---|---|---|---|---|---|---|---|---|---|---|
| Example 1 | Oleic acid | Dodecanethiol | — | 0.1 | 10 | O, Zn, S | 0.20 | 0.30 | Present | Present | 0.17 | 85 | 55 |
| Example 2 | Oleic acid | Dodecanethiol | — | 0.5 | 100 | O, Zn, S | 0.21 | 0.39 | Present | Present | 0.22 | 85 | 71 |
| Example 3 | Oleic acid | Dodecanethiol | — | 1.0 | 200 | O, Zn, S | 0.52 | 0.72 | Present | Present | 0.34 | 85 | 75 |
| Example 4 | Oleic acid | Dodecanethiol | — | 1.5 | 300 | O, Zn, S | 0.76 | 1.05 | Present | Present | 0.42 | 85 | 72 |
| Example 5 | Oleic acid | Dodecanethiol | — | 10.0 | 1000 | O, Zn, S | 0.80 | 1.10 | Present | Present | 0.66 | 85 | 62 |
| Comparative Example 1 | — | — | — | — | — | Zn, S | — | — | Present | Absent | — | 85 | 51 |
| Comparative Example 2 | — | Dodecanethiol | Oleylamine | — | — | Zn, S | — | — | Present | Absent | — | 85 | 48 |
| Comparative Example 3 | — | — | Oleylamine | — | — | Zn, S | — | — | Present | Absent | — | 85 | 44 |

From the results listed in Table 1, it was understood that the emission efficiency after the irradiation with ultraviolet rays was decreased and the durability was degraded in a case of the semiconductor nanoparticles in which oxygen atoms were not detected by XPS and the peak ($I_{COO}$) was not detected by FT-IR (Comparative Examples 1 to 3).

On the contrary, it was understood that the emission efficiency was high and the emission efficiency after the irradiation with ultraviolet rays was maintained to be higher than that in the comparative examples in a case of the semiconductor nanoparticles in which oxygen, zinc, and sulfur were detected by XPS and the peak ($I_{CH3}$) and the peak ($I_{COO}$) were detected by FT-IR (Examples 1 to 5).

Particularly, it was understood that the emission efficiency after the irradiation with ultraviolet rays was high and the durability was further excellent in a case where the ratio ($I_{COO}/I_{CH3}$) of the peak intensity between the peak ($I_{CH3}$) and the peak ($I_{COO}$) detected by FT-IR was in a range of 0.22 to 0.42 (Examples 2 to 4).

What is claimed is:

1. A semiconductor nanoparticle,
   wherein oxygen, zinc, and sulfur are detected by X-ray photoelectron spectroscopy analysis, and
   wherein two or more kinds of ligands are coordinated,
   wherein both of a ligand A which is represented by Formula (A) and contains a carboxyl group and a ligand B which is represented by Formula (B) and contains a mercapto group are coordinated,

$$R^1\text{—COOH} \tag{A}$$

$$R^2\text{—SH} \tag{B}$$

where $R^1$ and $R^2$ in Formulae (A) and (B) each independently represent an organic group, and
   wherein both of $R^1$ and $R^2$ in Formulae (A) and (B) represent a linear aliphatic hydrocarbon group.

2. The semiconductor nanoparticle according to claim 1, wherein a ratio of peak intensity between the peak ($I_{CH3}$) and the peak ($I_{COO}$) satisfies Formula (3)

$$0.22 \leq I_{COO}/I_{CH3} \leq 0.42 \tag{3}.$$

3. The semiconductor nanoparticle according to claim 1, wherein both of $R^1$ and $R^2$ in Formulae (A) and (B) represent an aliphatic hydrocarbon group having 8 to 25 carbon atoms.

4. The semiconductor nanoparticle according to claim 1,
wherein the ligand A is at least one ligand selected from the group consisting of decanoic acid, lauric acid, myristic acid, palmitic acid, stearic acid, behenic acid, oleic acid, and erucic acid, and the ligand B is at least one ligand selected from the group consisting of dodecanethiol, octanethiol, decanethiol, tetradecanethiol, hexadecanethiol, HS—(CH2)m-OH (in the formula, m represents an integer of 11 to 16), and HS—(CH2)m-(O—CH2CH2)n-OCH3 (in the formula, m represents an integer of 11 to 16, and n represents an integer of 3 to 6).

5. The semiconductor nanoparticle according to claim 4, wherein the ligand A is oleic acid, and
the ligand B is dodecanethiol.

6. The semiconductor nanoparticle according to claim 1, comprising:
a core which contains a Group III element and a Group V element; and
a shell which contains a Group II element and a Group VI element that cover at least a part of a surface of the core.

7. The semiconductor nanoparticle according to claim 6, wherein the Group III element contained in the core is In, and
the group V element contained in the core is any of P, N, and As.

8. The semiconductor nanoparticle according to claim 7, wherein the Group III element contained in the core is In, and
the Group V element contained in the core is P.

9. The semiconductor nanoparticle according to claim 6, wherein the core further contains a Group II element.

10. The semiconductor nanoparticle according to claim 9, wherein the Group II element contained in the core is Zn.

11. The semiconductor nanoparticle according to claim 1, comprising:
a core which contains a Group III element and a Group V element;
a first shell which covers at least a part of a surface of the core; and
a second shell which covers at least a part of the first shell.

12. The semiconductor nanoparticle according to claim 11,
wherein the first shell contains a Group II element or a Group III element,
where, in a case where the first shell contains a Group III element, the Group III element contained in the first shell is a Group III element different from the Group III element contained in the core.

13. The semiconductor nanoparticle according to claim 11,
wherein the first shell is a Group II-VI semiconductor which contains a Group II element and a Group VI element or a Group III-V semiconductor which contains a Group III element and a Group V element,
where, in a case where the first shell is the Group III-V semiconductor, the Group III element contained in the Group III-V semiconductor is a Group III element different from the Group III element contained in the core.

14. The semiconductor nanoparticle according to claim 13,
wherein, in a case where the first shell is the Group II-VI semiconductor, the Group II element is Zn and the Group VI element is Se or S, and in a case where the first shell is the Group III-V semiconductor, the Group III element is Ga and the Group V element is P.

15. The semiconductor nanoparticle according to claim 13,
wherein the first shell is the Group III-V semiconductor,
the Group III element is Ga, and
the Group V element is P.

16. The semiconductor nanoparticle according to claim 11,
wherein the second shell is a Group II-VI semiconductor which contains a Group II element and a Group VI element or a Group III-V semiconductor which contains a Group III element and a Group V element.

17. The semiconductor nanoparticle according to claim 16,
wherein the second shell is the Group II-VI semiconductor,
the Group II element is Zn, and
the Group VI element is S.

18. The semiconductor nanoparticle according to claim 11,
wherein the core, the first shell, and the second shell are respectively a crystal system having a zinc blende structure.

19. The semiconductor nanoparticle according to claim 11,
wherein, among the core, the first shell, and the second shell, a band gap of the core is the smallest, and
the core and the first shell respectively have a type 1 band structure.

20. A dispersion liquid comprising:
the semiconductor nanoparticle according to claim 1.

21. A film comprising:
the semiconductor nanoparticle according to claim 1.

22. A method of producing a semiconductor nanoparticle for synthesizing the semiconductor nanoparticle according to claim 1, comprising:
a mixing step of mixing a semiconductor nanoparticle QD to which one or both of a ligand A which is represented by Formula (A) and contains a carboxyl group and a ligand B which is represented by Formula (B) and contains a mercapto group are not coordinated, the ligand A, and the ligand B, $$R^1—COOH \qquad (A)$$

$$R^2—SH \qquad (B)$$

where $R^1$ and $R^2$ in Formulae (A) and (B) each independently represent an organic group,
wherein both of $R^1$ and $R^2$ in Formulae (A) and (B) represent a linear aliphatic hydrocarbon group.

23. The method of producing a semiconductor nanoparticle according to claim 22,
wherein the semiconductor nanoparticle QD, the ligand A, and the ligand B are mixed at a molar ratio that satisfies Formulae (4) and (5)

$$0.1 \leq (\text{ligand } A/\text{ligand } B) \leq 10 \qquad (4)$$

$$10 \leq \{\text{semiconductor nanoparticle } QD/(\text{ligand } A/\text{ligand } B)\} \leq 1000 \qquad (5).$$

24. The method of producing a semiconductor nanoparticle according to claim 22,
wherein the semiconductor nanoparticle QD, the ligand A, and the ligand B are mixed at a molar ratio that satisfies Formulae (4') and (5')

$$0.5 \leq (\text{ligand } A/\text{ligand } B) \leq 5 \quad (4')$$

$$100 \leq \{\text{semiconductor nanoparticle } QD/(\text{ligand } A/\text{ligand } B)\} \leq 300 \quad (5').$$

25. The method of producing a semiconductor nanoparticle according to claim 22,
wherein the semiconductor nanoparticle QD, the ligand A, and the ligand B are mixed in a temperature range of 20° C. to 100° C.

26. The method of producing a semiconductor nanoparticle according to claim 22,
wherein the semiconductor nanoparticle QD, the ligand A, and the ligand B are mixed under a light shielding condition and/or in a nitrogen atmosphere.

27. The method of producing a semiconductor nanoparticle according to claim 22,
wherein the mixing step is performed for 8 hours or longer.

28. The method of producing a semiconductor nanoparticle according to claim 22, further comprising:
a step of leaving the mixture to rest for 8 hours or longer after the mixing step.

* * * * *